(12) United States Patent
Imboden

(10) Patent No.: US 11,771,822 B1
(45) Date of Patent: Oct. 3, 2023

(54) WEARABLE DRUG DELIVERY SYSTEM

(71) Applicant: John Imboden, Olive Branch, MS (US)

(72) Inventor: John Imboden, Olive Branch, MS (US)

( * ) Notice: Subject to any disclaimer, the term of this patent is extended or adjusted under 35 U.S.C. 154(b) by 164 days.

(21) Appl. No.: 17/114,760

(22) Filed: Dec. 8, 2020

Related U.S. Application Data

(60) Provisional application No. 62/945,605, filed on Dec. 9, 2019.

(51) Int. Cl.
*A61M 5/142* (2006.01)
*A61M 5/172* (2006.01)
*A61M 5/168* (2006.01)

(52) U.S. Cl.
CPC .... *A61M 5/14244* (2013.01); *A61M 5/16881* (2013.01); *A61M 5/172* (2013.01); *A61M 2005/14252* (2013.01); *A61M 2209/088* (2013.01)

(58) Field of Classification Search
CPC .......... A61M 5/14244; A61M 5/16804; A61M 5/16877; A61M 5/16881; A61M 5/172; A61M 2005/14252; A61M 2209/088
See application file for complete search history.

(56) References Cited

U.S. PATENT DOCUMENTS

| | | | | |
|---|---|---|---|---|
| 4,741,736 A * | 5/1988 | Brown | ............. | A61M 5/172 D24/111 |
| 5,011,378 A * | 4/1991 | Brown | ............. | A61M 5/142 417/474 |
| 5,057,076 A * | 10/1991 | Polaschegg | ....... | A61M 5/16827 128/DIG. 13 |
| 5,478,211 A * | 12/1995 | Dominiak | ........... | A61M 39/281 607/153 |
| 5,558,639 A * | 9/1996 | Gangemi | .......... | A61M 5/16854 604/152 |
| 6,270,478 B1 * | 8/2001 | Mernøe | ............. | A61M 5/14244 604/122 |
| 8,568,360 B2 * | 10/2013 | Steinbach | ......... | A61M 5/14586 604/151 |
| 8,945,074 B2 * | 2/2015 | Buan | ....................... | A61M 1/96 604/320 |
| 9,616,171 B2 * | 4/2017 | Qin | ........................ | B32B 37/12 |
| 9,987,406 B2 * | 6/2018 | Wright | .................. | A61M 1/342 |
| 10,507,319 B2 * | 12/2019 | Haury | ................. | A61M 5/1407 |
| 11,324,881 B2 * | 5/2022 | Larson | .............. | A61M 5/14244 |

\* cited by examiner

*Primary Examiner* — Quynh-Nhu H. Vu
(74) *Attorney, Agent, or Firm* — The Patent Professor, P.A.; John Rizvi

(57) ABSTRACT

The present invention is directed to a safe and efficient, wearable drug delivery system for delivering one or more drugs directly into a patient's body in a prescribed manner. The wearable drug delivery system includes a drug delivery module including at least one receptor port for receiving and retaining a source of drugs, a skin base attachable to the drug delivery module and containing at least one corresponding drug delivery port for receipt of drugs from the at least one receptor port and a drug-dispensing nozzle for delivering the drug into the patient's system (e.g., into a vein). The drug delivery system additionally includes an electronic control system having a control module and an electronic valve, which may be positioned between the receptor port and the drug delivery port, for control of the flow of the drug in response to input from the control module.

19 Claims, 12 Drawing Sheets

WEARABLE DRUG DELIVERY SYSTEM

CROSS-REFERENCE TO RELATED APPLICATIONS

This application claims the benefit of U.S. Provisional Patent Application No. 62/945,605, filed on Dec. 9, 2019, which is incorporated herein by reference in its entirety.

FIELD OF THE INVENTION

The present invention relates generally to drug delivery devices, and more particularly, to a wearable drug delivery device to safely and efficiently deliver one or more drugs into a patient's system in a controlled and prescribed manner.

BACKGROUND OF THE INVENTION

During certain medical situations, it is often necessary to provide patients with a portable device for delivering drugs into their system outside of a medical facility. Such situations may include the frequent delivery of anti-addiction drugs, system boosters such as insulin injections, and the like. Many of the drugs need to be administered over prescribed periods of time and in particular order to be safe and effective.

Typically, the out of facility drug delivery devices are provided in the form of syringes, drug treated pads, etc. for injection or absorption of a single drug. In the case of syringes, the drug is delivered over a short period of time in a single dose. The use of syringes by patients to deliver drugs is often expensive, cumbersome and can be dangerous to the user or others if not closely controlled. In fact, many users or patients are not able to self-administer drugs using a syringe, and professional assistance is required, which may be time-consuming and costly for the user. In turn, the use of pads containing a drug which can be absorbed over a period of time is an improvement over the use of the syringes, but the rate of delivery may not be exact resulting an in over- or under-drugged conditions. Additionally, neither the use of syringes nor the pads can provide for a controlled release of several different drugs independently or in combination over a period of time.

Accordingly, there is a need for a solution to at least one of the aforementioned problems or goals above. For instance, there is an established need for a personal and wearable drug delivery system that can safely and effectively administer one or more doses of a drug or one or more drugs to a patient in a prescribed manner.

SUMMARY OF THE INVENTION

The present invention is directed to a safe and efficient, wearable drug delivery system for delivering one or more drugs directly into a patient's body in a prescribed manner. The wearable drug delivery system includes a drug delivery module including at least one receptor port for receiving and retaining a source of drugs, a skin base attachable to the drug delivery module and containing at least one corresponding drug delivery port for receipt of drugs from the at least one receptor port and a drug-dispensing nozzle for delivering the drug into the patient's system. The drug delivery system may additionally include an electronic control system having a control module and an electronic valve, positioned between the receptor port and the drug delivery port, for control of the flow of the drug therebetween in response to input from the control module.

In a first implementation of the invention, a wearable drug delivery system for delivering one or more drugs to a subject's body may comprise a skin base configured to attach to a subject's body, and a drug delivery module carried by the skin base. The skin base may include a drug-dispensing nozzle and one or more drug delivery ports. Each drug delivery port may be in fluid communication with the drug-dispensing nozzle via one or more channels formed in the skin base. The drug delivery module may include one or more receptor ports for the connection thereto of a respective container containing a drug. Each receptor port may be provided with a piercing pin configured to pierce said respective container. The wearable drug delivery system may further include an electronic control system comprising a control module and one or more electronically controlled valves operatively connected to the control module. Each electronically controlled valve may be configured to regulate fluid communication from the piercing pin of a respective receptor port of the one or more receptor ports to the drug-dispensing nozzle responsively to a signal from the control module.

In a second aspect, the drug delivery module may be disconnectably mountable to the skin base.

In another aspect, the drug delivery module and skin base may be flexible and configured to conform to the subject's body.

In another aspect, each one of the drug delivery module and skin base may be formed as a flexible panel.

In another aspect, the one or more drug delivery ports may include a plurality of drug delivery ports, and the one or more receptor ports may include a plurality of receptor ports corresponding in number to the plurality of drug delivery ports.

In yet another aspect, the electronic control system may be located within the drug delivery module.

In another aspect, each electronically controlled valve may be arranged between the respective receptor port and a respective drug delivery port of the one or more drug delivery ports.

In another aspect, the drug delivery module may include one or more activation switches. Each activation switch may be associated to a respective receptor port of the one or more receptor ports and to a respective electronically controlled valve of the one or more electronically controlled valves. Furthermore, each activation switch may be operable between a first position and a second position to respectively prevent and allow fluid communication from the piercing pin of said respective receptor port to the drug-dispensing nozzle.

In another aspect, the drug delivery module may include one or more nozzles. Each nozzle may be configured to couple with a respective drug delivery port of the one or more drug delivery ports of the skin base. Each nozzle may include a nozzle pin in fluid communication the piercing pin of a respective receptor port of the one or more receptor ports of the drug delivery module.

In yet another aspect, the one or more receptor ports may be arranged on a first side of the drug delivery module and the one or more nozzles may be arranged on a second side of the drug delivery module, the second side arranged opposite to the first side.

In another aspect, the second side of the drug delivery module may be arranged facing the skin base.

In another aspect, the second side of the drug delivery module may be arranged facing a first side of the skin base.

The skin base may further include a second side opposite to the first side of the skin base, and the second side of the skin base may be configured to face a subject's skin.

In another aspect, the second side of the skin base may be configured to adhere to the subject's skin.

In yet another aspect, the drug-dispensing nozzle may include a needle.

In another aspect, the drug delivery module may include one or more retainer straps. Each retainer strap may be attachable to the drug delivery module in a securing position in which the retainer strap secures said respective container to the drug delivery module while the respective container is pierced by the piercing pin of a respective receptor port.

In another aspect, the one or more retainer straps may be configured to further adopt a storage position in which the one or more retainer straps are detachably attached to an area of the drug delivery module separate from said one or more receptor ports.

In another aspect, at least one retainer strap may be stretchable. When the stretchable retainer strap is arranged in the securing position, the retainer strap may be stretched to compress the respective container while the respective container is pierced by the piercing pin of a receptor port of the one or more receptor ports.

In yet another aspect, the system may further include a body-securing strap configured to attach to a subject's body. The skin base may be carried by the body-securing strap.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a convenient and efficient wearable drug delivery system that is capable of automatically delivering one or more drugs from drug repositories positioned on the drug delivery system and administering them to a patient.

Figure 1:
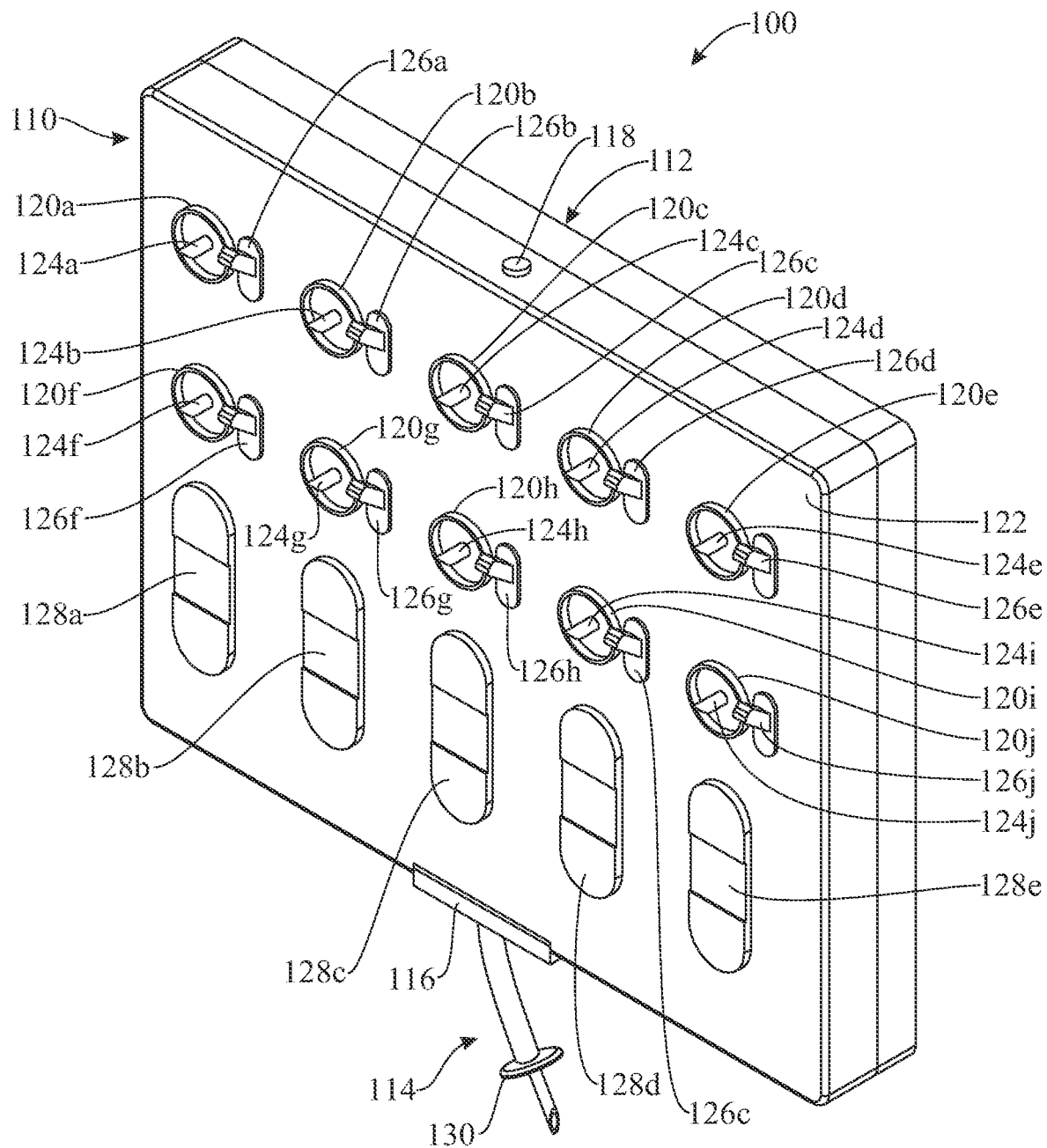
FIG. 1 presents a top, front isometric view of a wearable drug delivery system in accordance with an illustrative embodiment of the present invention.
Figure 2:
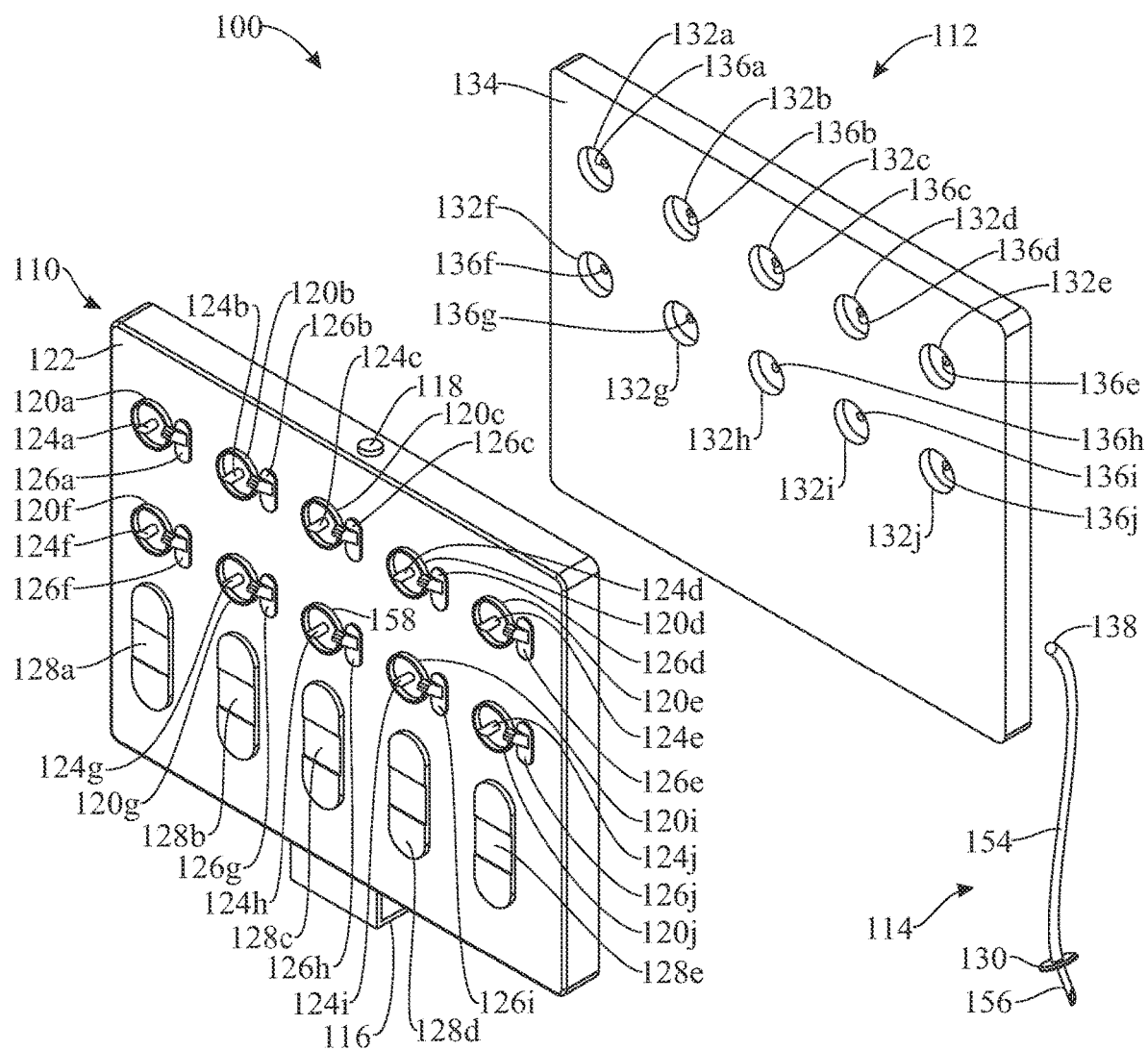
FIG. 2 presents a top, front isometric view, with parts separated, of the wearable drug delivery system of FIG. 1 including a drug delivery module, a skin base and a drug-dispensing nozzle.

Referring initially to FIGS. 1 and 2, a wearable drug delivery system 100 is illustrated in accordance with an exemplary embodiment of the present invention, configured as an automatically-operable drug delivery system. As shown, the drug delivery system 100 generally includes a drug delivery module 110 and a skin base 112. The skin base 112 is attachable to the drug delivery module 110 and configured to carry the drug delivery module 110 and secure the drug delivery module 110 to a patient's body. The drug delivery system 100 further includes a drug-dispensing tubing or nozzle 114, such as to dispense a drug into a subject's vein, the drug-dispensing nozzle 114 extending from the skin base 112 for transmitting drugs supplied by the drug delivery system 100 through the drug delivery module 112, into a patient's body. In some embodiments, a latch 116 is provided to secure the drug delivery module 110 to the skin base 112. The skin base 112 may include a corresponding notch (not shown) for receipt of the latch 116. A power switch 118 may be provided on the drug delivery module to initiate activation of the drug delivery system 100 as will be described in detail hereinafter.

The drug delivery module 110 and the skin base 112 operate together and are formed generally as two parallel, relatively thin panels arranged adjacent to one another. In some embodiments, the drug delivery module 110, and more preferably, both the drug delivery module 110 and the skin base 112, may be made of a flexible material to allow the drug delivery system 100 to deformably conform to a patient's body part such as an arm, leg or neck. The drug delivery module 110 and skin base 112 may be formed from a variety of flexible materials such as, but not limited to, natural or synthetic rubber, silicone, various polymers, etc. The drug-dispensing nozzle 114 is hollow and is preferably formed from a graphene material as discussed in more detail hereinbelow. As shown for instance in FIG. 1, a stop or skin pad 130 may be provided on the drug-dispensing nozzle 114 to limit the depth of insertion of the drug-dispensing nozzle into the patient and provide a means of securing the drug-dispensing nozzle 114 to the patient. In some embodiments, the drug-dispensing nozzle 114 may terminate in a needle or other similar item configured to facilitate fluid communication with the patient or subject's vein.

As shown in FIG. 1, the drug delivery module 110 includes a plurality of receptor ports 120a-j which may be arranged in rows and columns along a front or first side 122 of the drug delivery module 110: for instance, the drug delivery module 110 specifically includes ten receptor ports 120a-j arranged in two rows across five columns. In some embodiments, such as the present embodiment, the receptor ports 120a-j may be formed as depressions or slight recesses in the first side 122 of the drug delivery module 110. The receptor ports 120a-j are provided to receive sources of similar or differing drugs and transmit the drugs through the drug-dispensing nozzle 114 into a patient. Hollow piercing pins 124a-j may be positioned within and extend outwardly from respective receptor ports 120a-j to pierce the sources of drugs and pass the drugs to the drug-dispensing nozzle 114. A plurality of activation switches 126a-j may be provided adjacent the respective receptor ports 120a-j on the first side 122 of the drug delivery module 110 and may be operable to actuate individual valves (e.g. valve 172 shown in FIG. 6) associated with each respective receptor port 120a-j to establish fluid communication from the respective piercing pin 124a-j towards the drug-dispensing nozzle 114, to allow for the flow of the drugs to the drug-dispensing nozzle 114 through the drug delivery system 100 and into the patient. The activation switches 126a-j may be in the form of manually operable switches, pressure pads or any other on/off type of activation device and the respective valves operated by the activation switches 126a-j (e.g., valve 172) may include any applicable fluid valve mechanism configured to selectively allow or prevent fluid communication responsively to user operation of the corresponding activation switch 126a-j.

In some embodiments, a plurality of flexible retainer straps 128, such as retainer straps 128a-e, may be releasably affixed (e.g., by an adhesive, hook-and-loop fastener, or other releasable attachment) to the first side 122 of the drug delivery module 110. The flexible retainer straps 128a-e are provided to secure the sources of drugs within the receptor ports 120a-j in a manner described in more detail hereinbelow and compress the sources of drugs within the receptor ports 120a-j. In some embodiments, the retainer straps 128a-e may be formed of a material that contracts when an electrical current is present and expands when the current is removed such that the retainer straps 128a-e can compress the source of drugs within the receptor ports 120a-j to assist in fully exhausting the drugs contained within the sources of drugs into the drug delivery system 100.

Referring specifically to FIG. 2, the skin base 112 is provided with a plurality of drug delivery ports 132a-j on a front or first side 134 of the skin base 112 and which correspond to the receptor ports 120a-j formed in the drug delivery module 110. The drug delivery ports 132a-j may be formed as recesses or depressions on said first side 134 of the skin base 112, as shown. Each of the drug delivery ports 132a-j includes a respective, centrally located passage port or hole 136a-j. The hole 136a-j of each drug delivery port 132a-j is in fluid communication with the piercing pin 124a-j of the respective receptor port 120a-j of the drug delivery module 110, and is also in fluid communication with the drug-dispensing nozzle 114. For instance, in the present embodiment, a first end 138 of the drug-dispensing nozzle 114 is in fluid communication the holes 136a-j of the drug delivery ports 132a-j.

Figure 3:
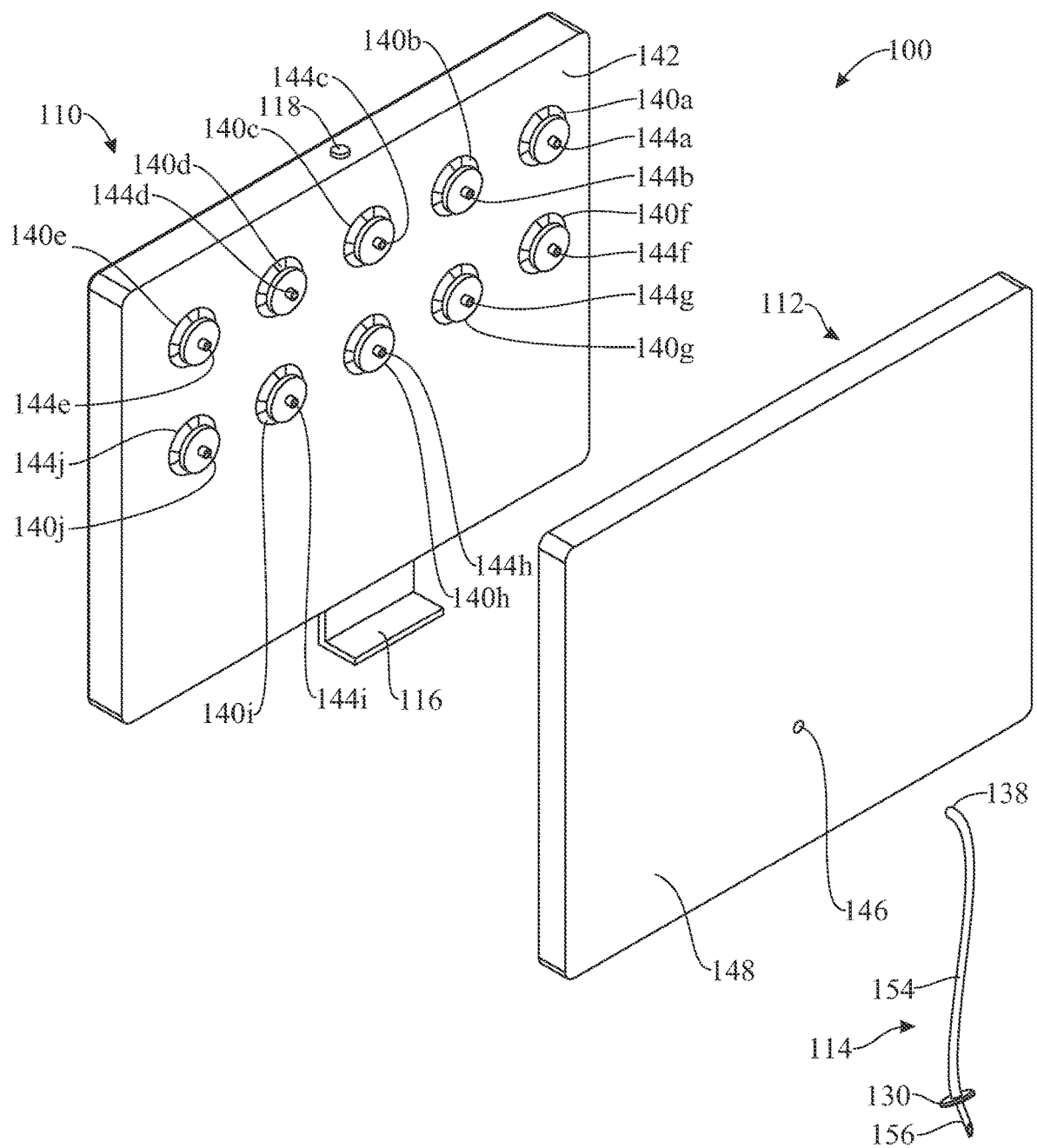
FIG. 3 presents a top, rear isometric view, with parts separated, of the wearable drug delivery system of FIG. 1.

Turning now to FIG. 3, a plurality of protrusions or nozzles 140a-j are provided on and extend from a rear or second side 142 of the drug delivery module 110, the second side 142 arranged opposite and optionally parallel to the first side 122 (FIG. 2) of the drug delivery module 110 and facing the first side 134 (FIG. 2) of the skin base 112. Respective hollow nozzle pins 144a-j extend from the nozzles 140a-j. The nozzles 140a-j extending from the second side 142 of the drug delivery module 110 are configured to extend into (be received within) the corresponding drug delivery ports 132a-j formed in the front or first side 134 of the skin base 112 (FIG. 2). The nozzle pins 144a-j on the rear or second side 142 of the drug delivery module 110 are configured to extend into the holes 136a-j (FIG. 2) of the drug deliver ports 132a-j formed in the skin base 112. When each nozzle pin 144a-j is inserted into the respective hole 136a-j, the nozzle pin 144a-j is in fluid communication with the drug-dispensing nozzle 114 through an outlet 146 formed in a rear or second side 148 of the skin base 112. Specifically, the first end 138 of the drug-dispensing nozzle 114 is connected to the second side 148 of the skin base 112 at the outlet 146.

As noted above, the drug-dispensing nozzle 114 may be formed of graphene and may include an elongate graphene tube 154 extending from the first end 138 of the drug-dispensing nozzle 114 to the skin pad 130. A hollow tissue piercing needle 156 may extend from the graphene tube 154 to penetrate tissue.

Figure 4:
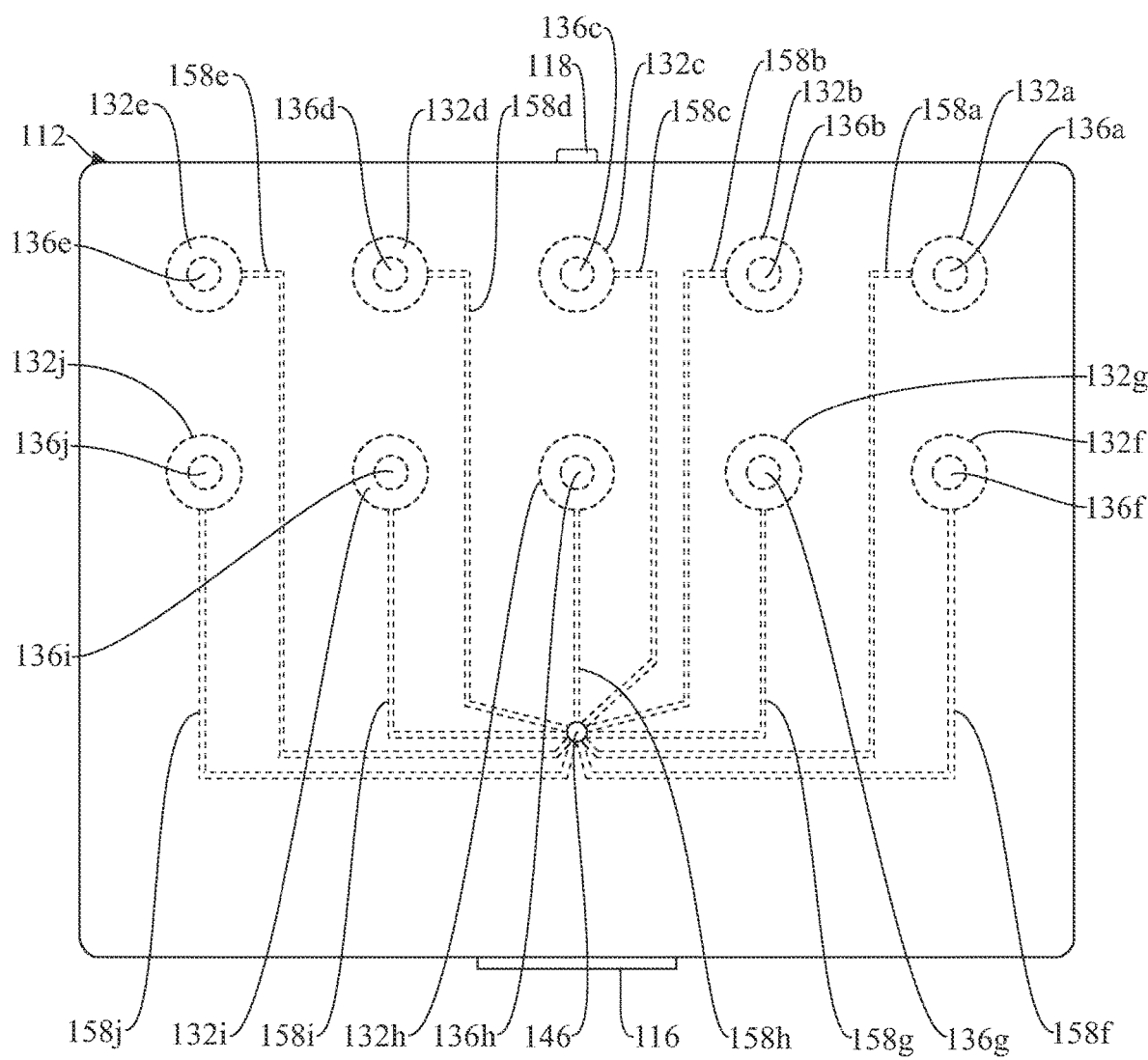
FIG. 4 presents a rear view of the skin base of the wearable drug delivery system of FIG. 1 with drug delivery channels shown in hidden (broken) lines.

As best shown in FIG. 4, the holes 136a-j of the drug delivery ports 132a-j on the first side 134 of the skin base 112 are in fluid communication with the outlet 146 located on the second side 148 of the skin base 112 through a plurality of drug delivery channels 158a-j formed within the skin base 112. Thus, the drug-dispensing nozzle 114 is in fluid communication with the drug delivery ports 132a-j (FIG. 2), and thus the receptor ports 120a-j on the drug delivery module 110, through the drug delivery channels 158a-j.

Figure 5:
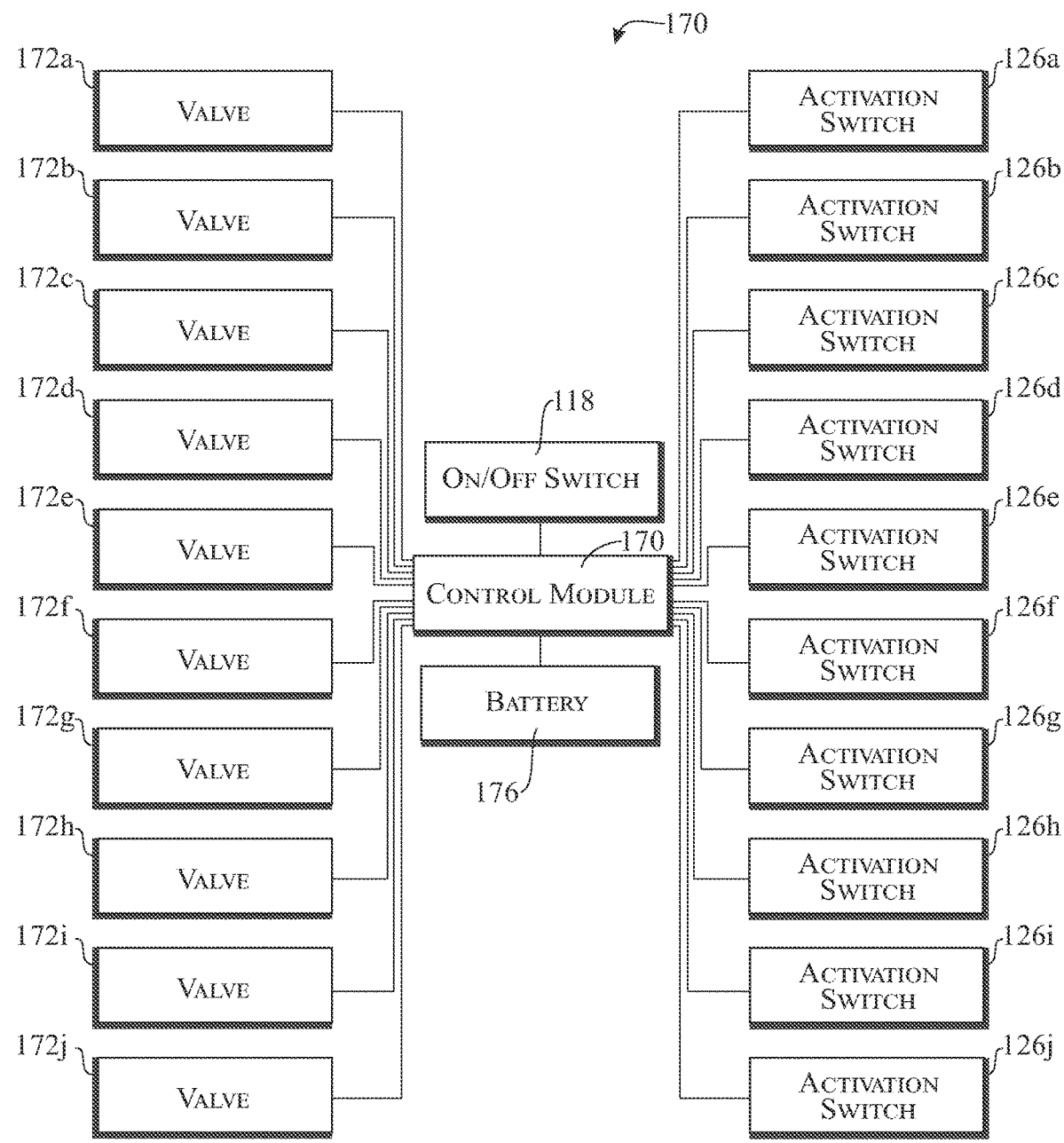
FIG. 5 presents a schematic view of an electronic control system of the wearable drug delivery system of FIG. 1.
Figure 6:
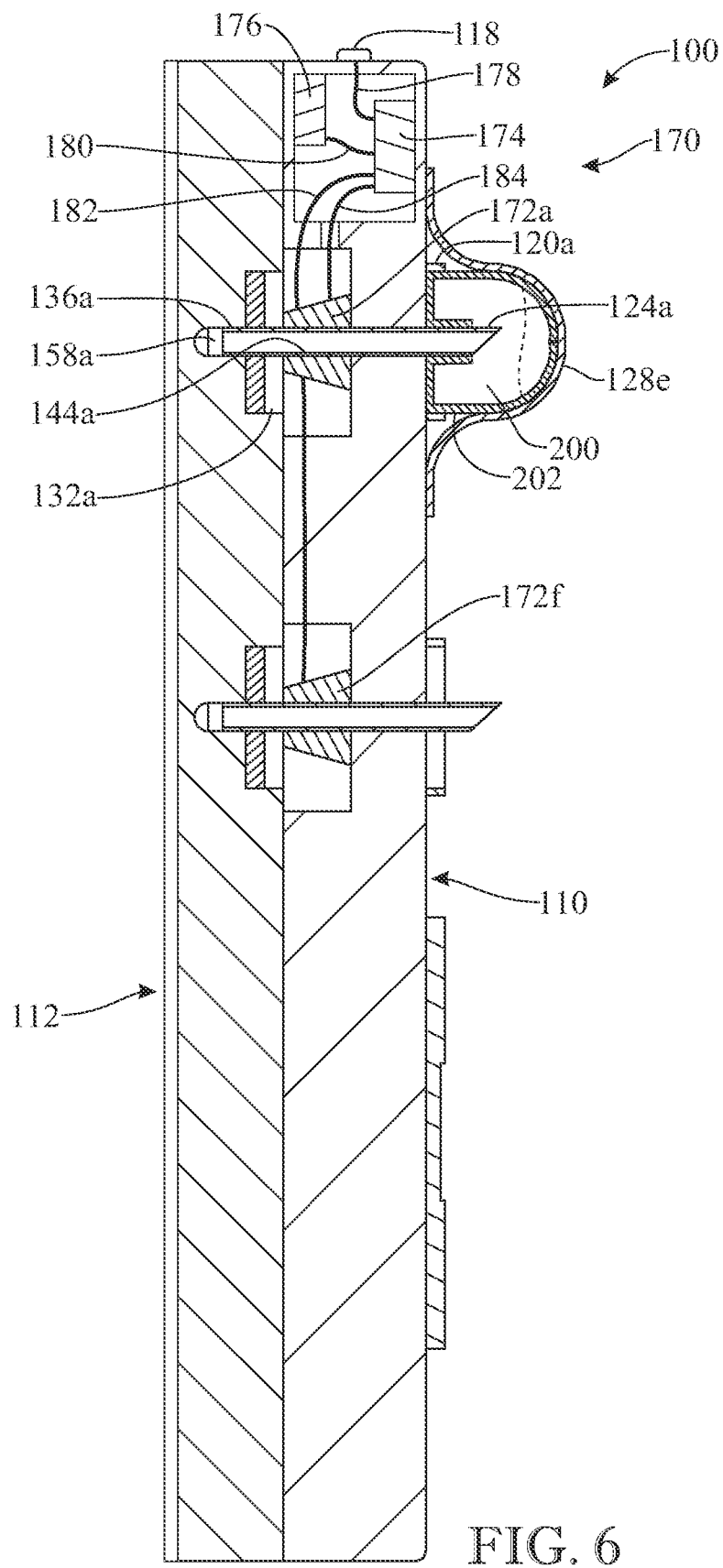
FIG. 6 presents a cross-sectional view, taken along section plane 6-6 of FIG. 1, of the wearable drug delivery system of FIG. 1.

Turning now to FIGS. 5 and 6, the drug delivery system 100 of the present embodiment includes an electronic control system 170. The electronic control system 170 is provided to control the locations from which drugs are drawn, i.e., the receptor ports 120a-j, as well as control the volume amount of each individual drug supplied to the drug-dispensing nozzle 114 and thus to the patient. The electronic control system 170 includes a plurality of electronic valves 172a-j associated with the respective receptor ports 120a-j in the drug delivery module 110 and the respective drug delivery ports 132a-j formed in the skin base 112.

The control system 170 includes a control module 174 which is in electronic communication with the electronic valves 172a-j as well as in electronic communication with the power switch 118 and the activation switches 126a-j. By incorporating the activation switches 126a-j into the control protocol, the activation switches 126a-j serve as safety mechanisms ensuring that the control system 170 does not attempt to draw from an empty receptor port 120 which could result in the injection of air or other contaminants into the patient's system.

The control module 174 is programmable such that the control module 174 can control which of the electronic valves 172a-j are open or closed to permit the flow of drugs therethrough as well as control the duration and amount of any individual drug passing through the electronic valves 172a-j. While not specifically shown, the drug delivery system 100 may include an on-board control center or panel (not shown), which may include a touch screen or other user interface, for programming the control module 174. In other embodiments, the control module 172 may be permanently programmed with a specific protocol or may be selectively programmed through an external system such as, but not limited to, a master computer, laptop, smartphone, etc. Further, the disclosed drug delivery system 100 may be provided with a wireless communications system, such as, but not limited to, infrared, radiofrequency, etc. to allow the control module 170 to be programmed wirelessly and remotely. An on-board battery system 176 is provided to power the control module 170 and the electronic valves 172a-j and may be user-replaceable or permanent and rechargeable, for instance and without limitation.

With specific reference to FIG. 6, the electronic control system 170 is illustrated in connection with the operation of the first receptor port 120a and drug delivery port 132a. The following discussion will be given with regard to the first or "a" set of components in the first row and column. The components associated with the remaining receptor ports 120b-j and respective drug delivery ports 132b-j function identically. The figure further shows that the power switch 118 is connected to the control module 174 through a wire 178 and the battery system 176 is connected to the control module 174 through a wire 180. Wires 182 and 184 connect the control module 174 to the first electronic valve 172a.

As shown, the piercing pin 124a extends through the receptor port 120a and is in fluid communication with the nozzle pin 144a. In different embodiments, the piercing pin 142a and the nozzle pin 144a may be formed separately or may be formed as a single hollow pin or tube. The combined piercing pin 142a and nozzle pin 144a pass through the electronic valve 172a which controls the flow of drugs therethrough. For instance, the electronic valve 172a may include an electrically-actuated shutter which is movable between a closed position in which the shutter extends into the fluid passageway provided by the combined piercing pin 142a and nozzle pin 144a blocking fluid flow therewithin, and an open position in which the shutter is moved out the fluid passageway provided by the combined piercing pin 142a and nozzle pin 144a allowing fluid flow therewithin. In other non-limiting examples, the electronic valve 172a may include a rotational valve mechanism (e.g., butterfly valve, ball valve, rotary valve, etc.) configured to rotate between an open position and a closed position configured to respectively allow and prevent fluid communication between the piercing pin 142a and the nozzle pin 144a. As noted hereinabove, the nozzle pin 144a is in fluid communication with the hole 132a of the drug delivery port 136a which in turn is in fluid communication with the drug delivery channel 158a and the outlet 146 (FIG. 4) and thus with the drug-dispensing nozzle 114.

Figure 7:
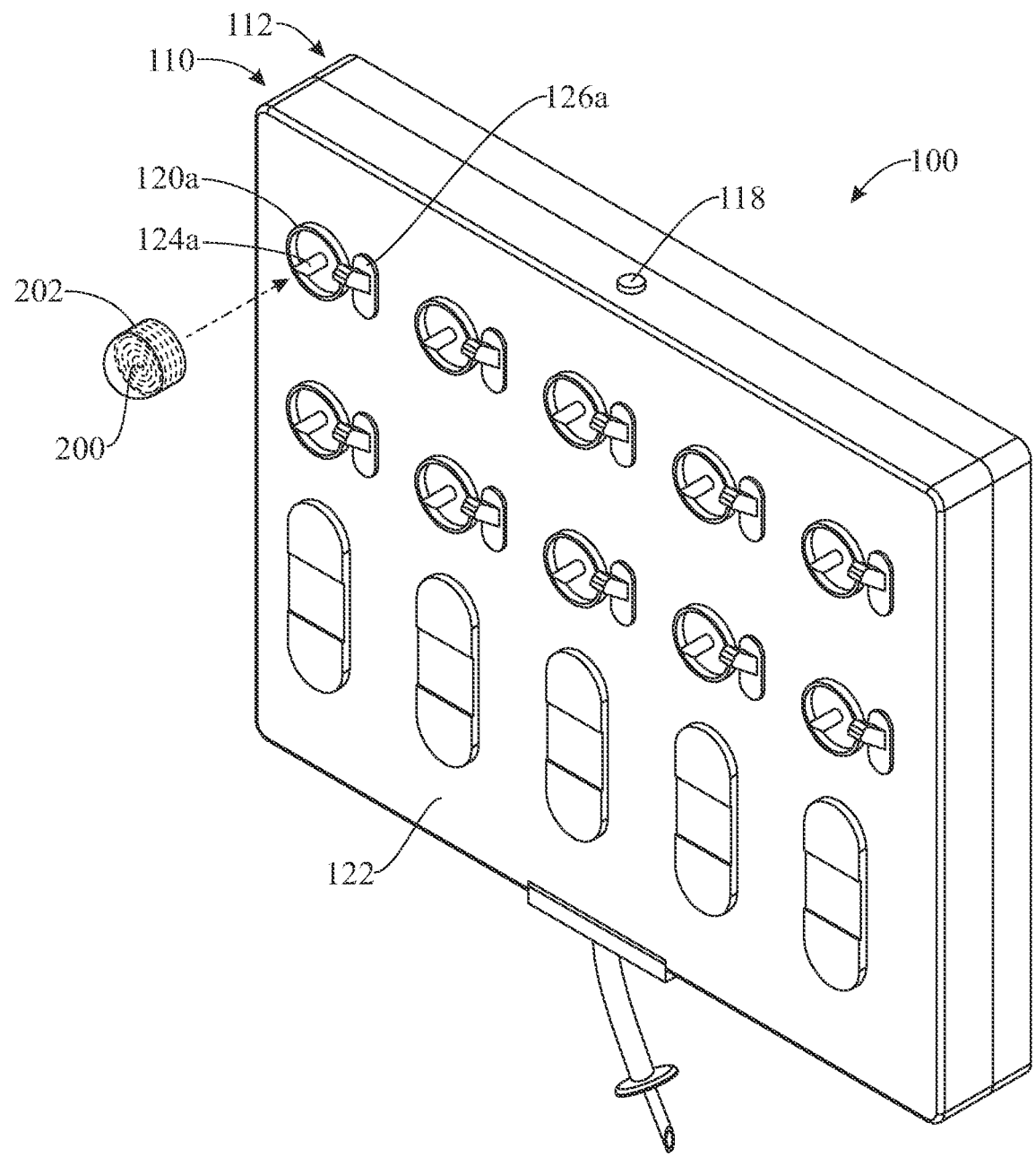
FIG. 7 presents a top, front isometric view of the wearable drug delivery system of FIG. 1 and a drug repository unit containing a drug to be delivered to a patient.

Turning now to FIGS. 7-11, and initially with regard to FIG. 7, the operation of the wearable drug delivery system 100 to deliver a drug, such as a drug 200 into a patient's body will now be described. The drug 200 is provided as a liquid contained within a penetrable drug capsule or repository 202. Initially, the power switch 118 is turned off and all the activation switches 126 are in a first or off position blocking flow of fluid through their respective receptor ports 120 for safety.

Figure 8:
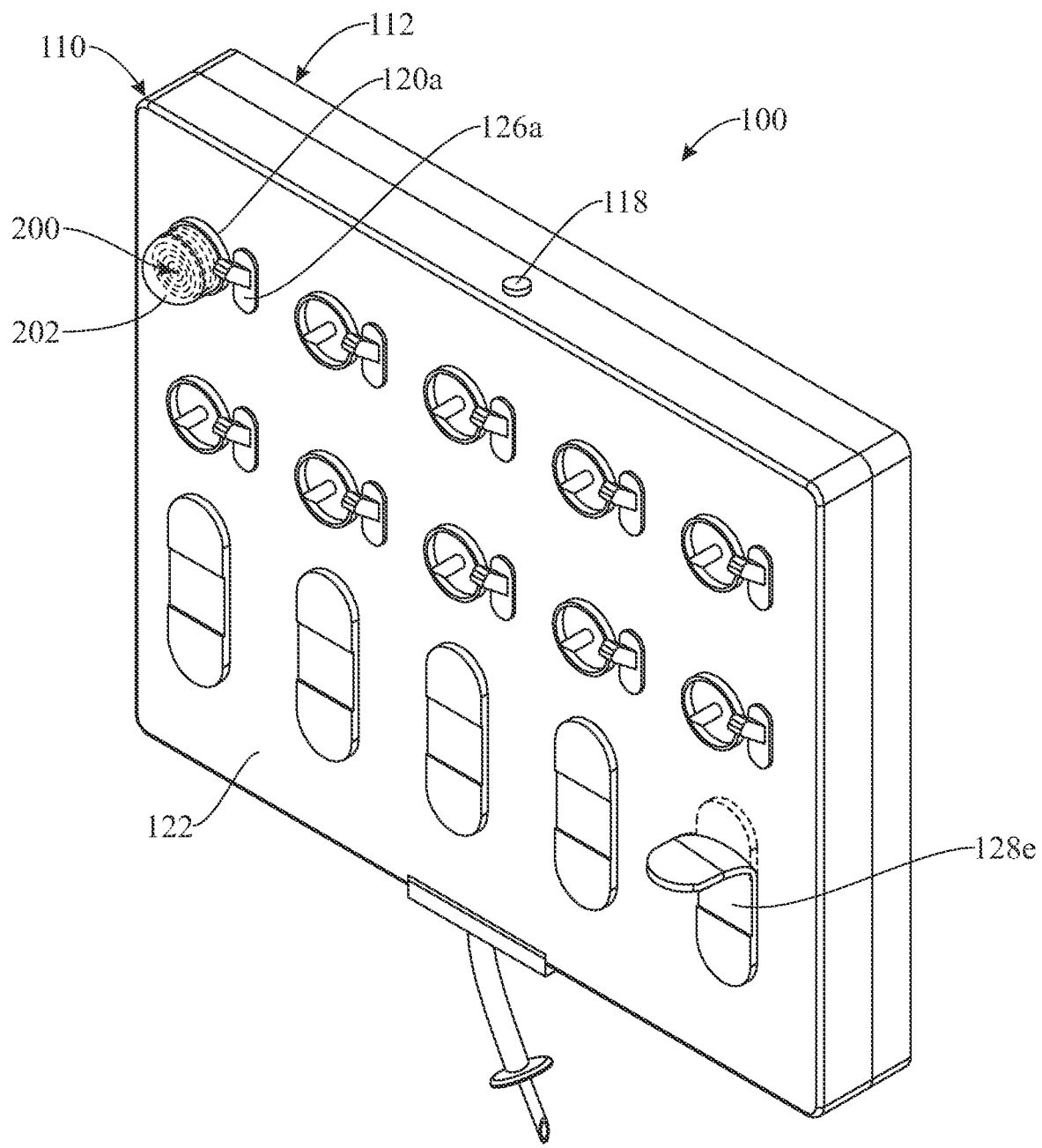
FIG. 8 presents a top, front isometric view of the wearable drug delivery system of FIG. 1 with the drug repository unit installed in a receptor port of the drug delivery system.
Figure 9:
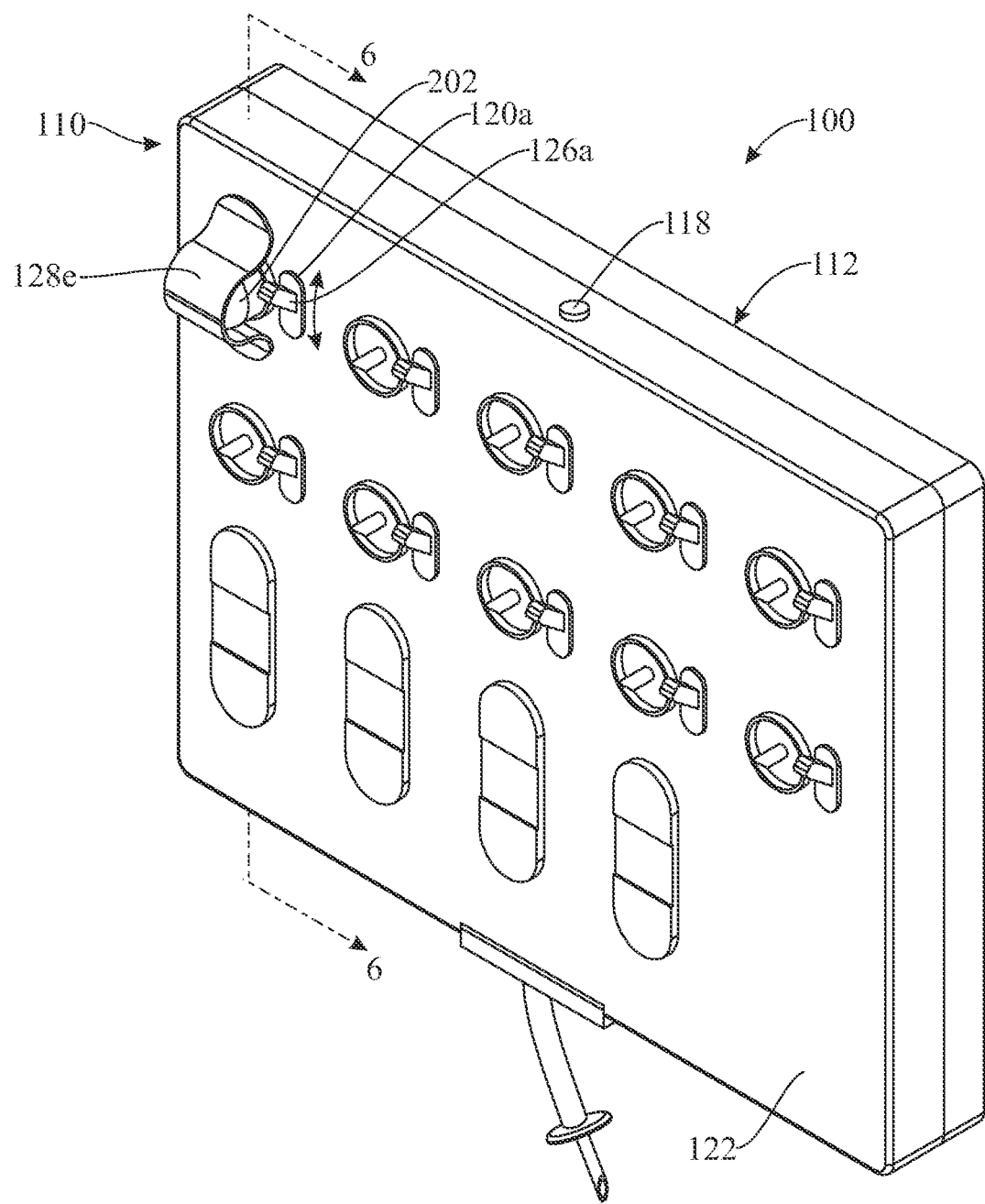
FIG. 9 presents a top, front isometric view of the wearable drug delivery system of FIG. 1 with a flexible retainer strap placed over the drug depository unit and secured to a drug delivery module of the flexible, wearable drug delivery system.

As shown in FIGS. 7 and 8, the drug repository 202, containing the desired drug 200, is positioned over the receptor port 120a and pressed into the receptor port 120a such that the piercing pin 124a penetrates the drug repository 202 to access the drug 200 contained therein. For instance, in some embodiments, the piercing pin 124a may perforate the drug repository 202. As noted above, the activation switch 126a is initially in the off position. A retainer strap 128, for example retainer strap 128e, may be removed from the first side 122 of the drug delivery module 110 and positioned over the drug repository 202 and attached to the first side 122 to secure the drug repository 202 in place in the receptor port 120a. As shown in FIG. 9, the retainer strap 128e may be attached to the first side 122 in a stretched configuration such that the retainer strap 128e tends to compress and thereby provides a source of compression to facilitate fully emptying the drug repository 202 of its drug 200 upon activation of the electronic control system 170.

Figure 10:
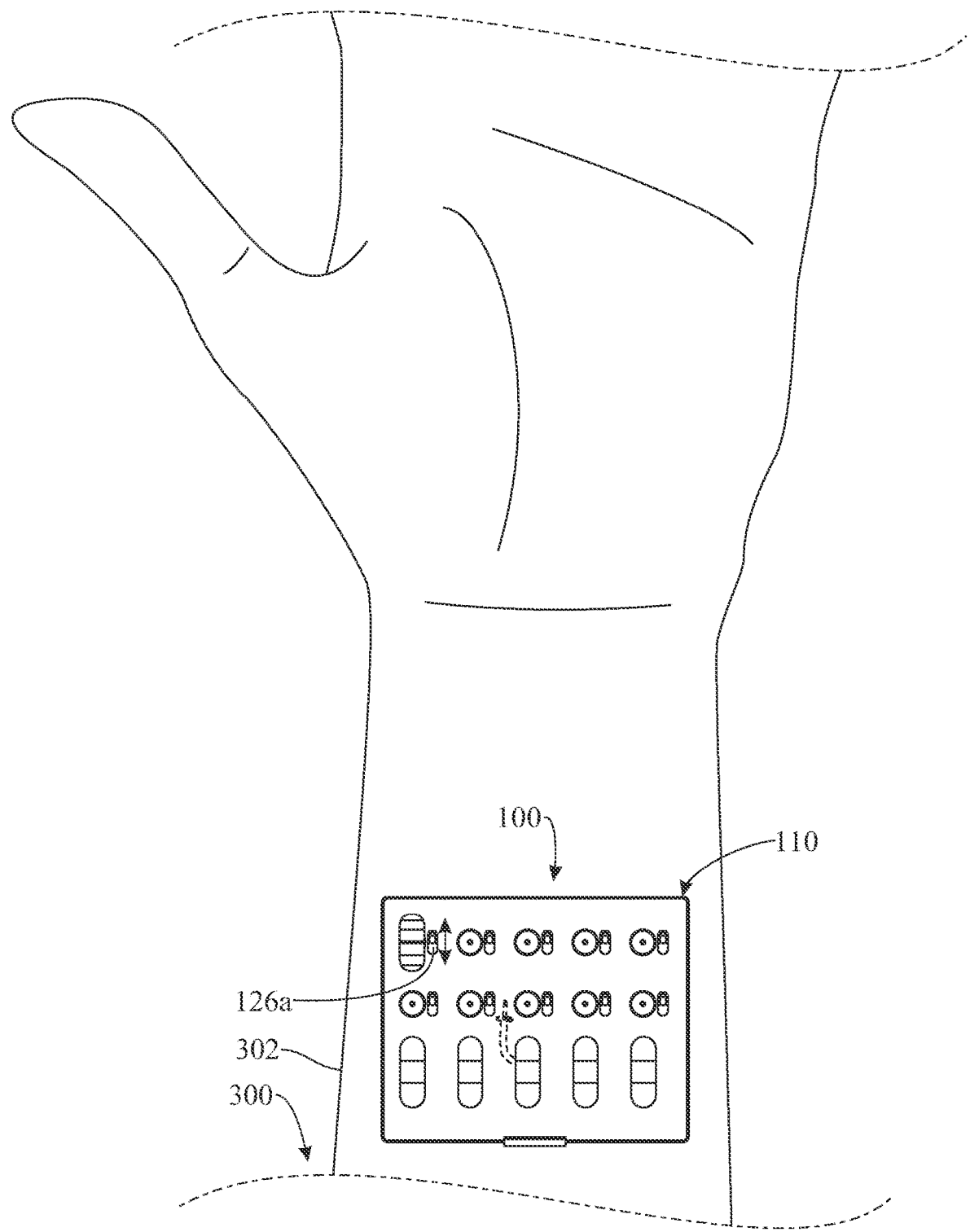
FIG. 10 presents a front isometric view of the wearable drug delivery system of FIG. 1 affixed to an inner forearm surface of a patient's arm.

As shown in FIG. 10, the drug delivery system 100 is then adhered or otherwise secured to a body part of a patient, such as the inner forearm 302 of the patient 300. In some embodiments, the rear or second side 148 of the skin base 112 may be provided with a bio-compatible adhesive configured to adhere to human or animal skin. As noted hereinabove, the disclosed wearable drug delivery system 100 and, in particular, the drug delivery module 110 and the skin base 112 may be flexible so as to conform to the shape of the body part of the patient 300. While not specifically shown, the hollow tissue piercing needle 156 of the drug-dispensing nozzle 114 is inserted into a vein of the patient 300 in combination with, or in advance to, adhering the drug delivery system 100 to the inner forearm 302 of the patient 300. Thereafter, the power switch 118 may be activated to arm the drug delivery system 100 and activate the control module 174 of the electronic control system 170. Once ready to administer the drug, the user may move the activation switch 126a to the second or open position to operate the electronic valve 172a and deliver the prescribed drug 200 into the patient 300. The remaining activation switches 126b-j remain in the closed condition or off position for safety.

It should be noted that other drug repositories containing more of the same drug or differing drugs can be loaded into the remaining receptor ports for delivery of additional drugs simultaneously, in various duration/amount combinations or sequentially into a patient's system. The control module 170 may operate the electronic valves 172a-j in predefined or preprogrammed sequences, which may be stored in a memory and executed by a processor comprised in the control module 170. In some embodiments, prior to executing a drug combination delivery sequence involving more than one electronic valve 172a-j, the control module 170 may first check that the activation switches 172a-j corresponding to said more than one electronic valve 172*a-j* involved in the sequence are in the activated or "on" position and, in some embodiments, may further check that the remaining activation switches 172*a-j* which are not involved in the sequence are in the "off" position, for further safety.

Thus, the wearable drug delivery system 100 provides a versatile, safe and efficient device for delivering one or more drugs into a patient's system in a prescribed manner.

Figure 11:
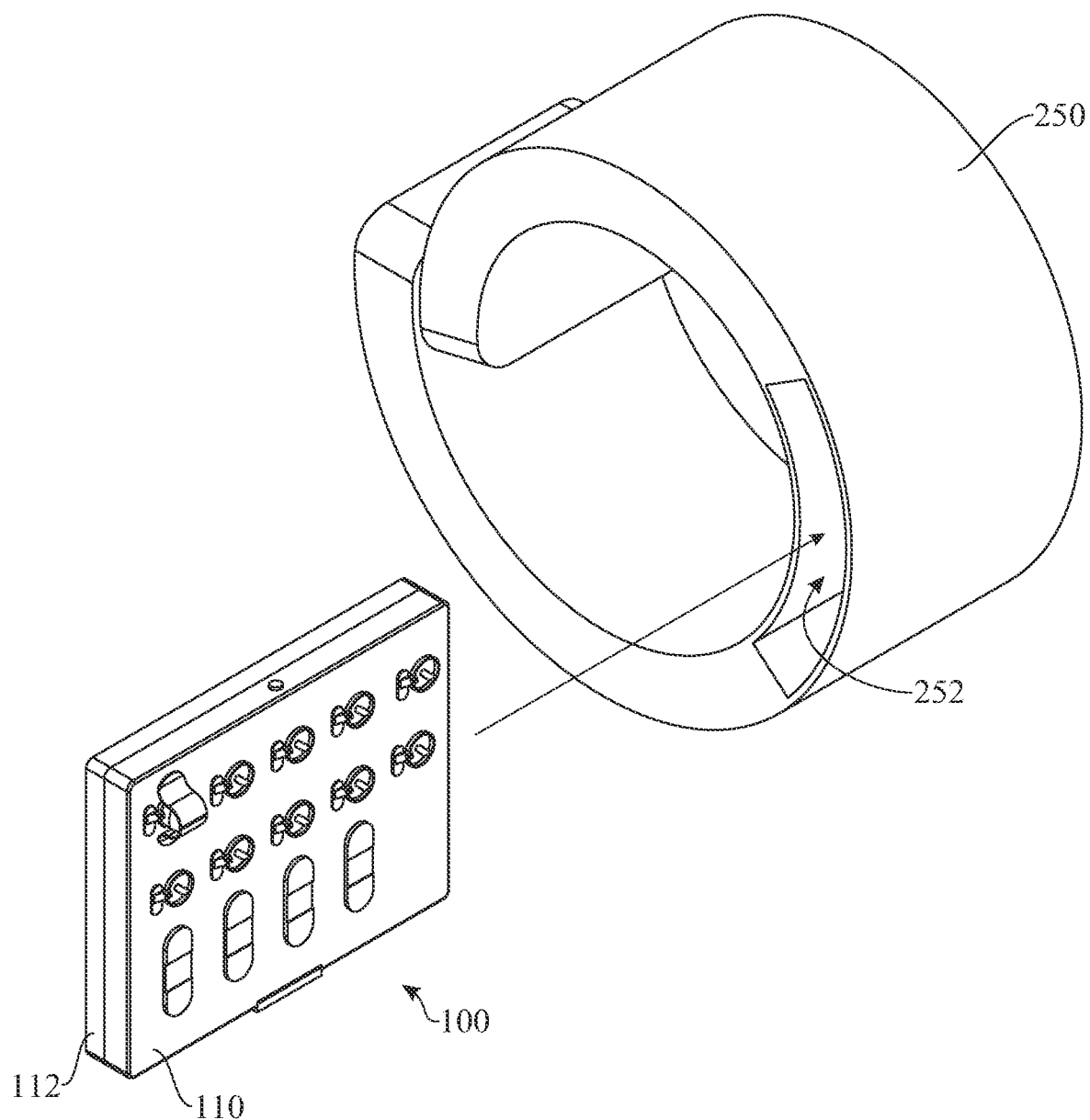
FIG. 11 presents a top, front isometric view of an auxiliary, flexible securing strap, having a compartment for receipt of the wearable drug delivery system of the present invention and the wearable drug delivery system of FIG. 1.
Figure 12:
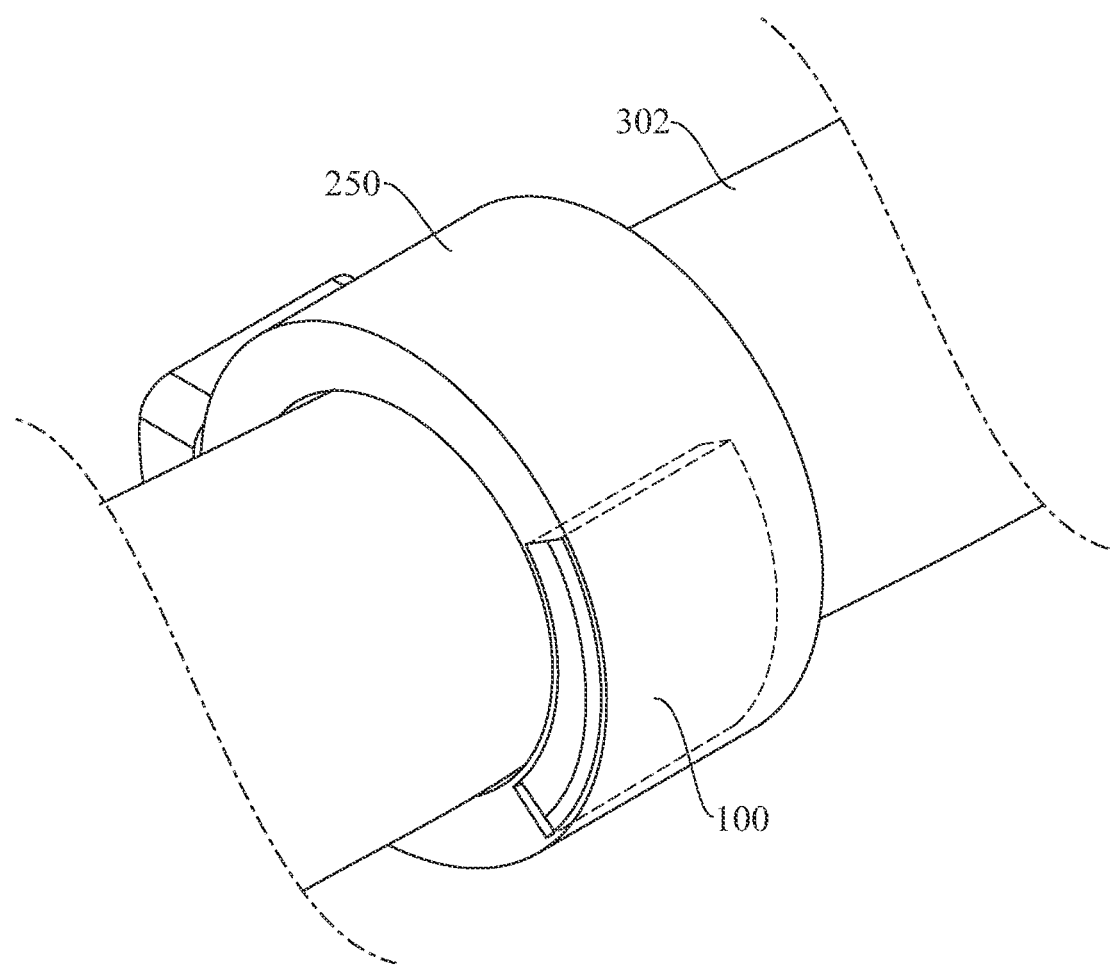
FIG. 12 presents a top, front isometric view of the auxiliary, flexible securing strap, with the wearable drug delivery system of FIG. 1 installed in the compartment, affixed about the arm of the patient.

Turning to FIGS. 11 and 12, there is disclosed an auxiliary flexible cuff or strap 250 in accordance with a further embodiment of the invention. The strap 250 may be provided to secure the drug delivery system 100 to an arm or other body part of the patient 300. The strap 250 is preferably flexible and contains a compartment 252 for receipt of the drug delivery system 100. The strap 250 may include securing devices such as, but not limited to, one or more buckles, hook-and-loop closure systems, etc., or may be self-adhering. In use, the drug delivery system 100 is inserted into the compartment 252 of the strap 250 and the strap 250 is secured about, for instance, the arm 302 of the patient 300. The drug-dispensing nozzle 114 is inserted into the patient's vein and the drug delivery system is operated as described hereinabove.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A wearable drug delivery system for delivering one or more drugs to a subject's body, comprising:
    a skin base configured to attach to a subject's body, the skin base comprising a drug-dispensing nozzle and one or more drug delivery ports, wherein each drug delivery port is in fluid communication with the drug-dispensing nozzle via one or more channels formed in the skin base;
    a drug delivery module carried by the skin base and comprising one or more receptor ports for the connection thereto of a respective container containing a drug, each receptor port comprising a piercing pin configured to pierce said respective container; wherein the drug delivery module and skin base are flexible and configured to conform to the subject's body; and
    an electronic control system comprising a control module and one or more electronically controlled valves operatively connected to the control module, wherein each electronically controlled valve is configured to regulate fluid communication from the piercing pin of a respective receptor port of the one or more receptor ports to the drug-dispensing nozzle responsively to a signal from the control module.

2. The system of claim 1, wherein the drug delivery module is disconnectably mountable to the skin base.

3. The system of claim 1, wherein the drug delivery module and skin base are each formed as a flexible panel.

4. The system of claim 1, wherein the one or more drug delivery ports comprise a plurality of drug delivery ports, and the one or more receptor ports comprise a plurality of receptor ports corresponding in number to the plurality of drug delivery ports.

5. The system of claim 1, wherein the electronic control system is located within the drug delivery module.

6. The system of claim 1, wherein said each electronically controlled valve is arranged between the respective receptor port and a respective drug delivery port of said one or more drug delivery ports.

7. The system of claim 1, wherein the drug delivery module comprises one or more activation switches, wherein each activation switch is associated to a respective receptor port of the one or more receptor ports and to a respective electronically controlled valve of the one or more electronically controlled valves and is operable between a first position and a second position to respectively prevent and allow fluid communication from said piercing pin of said respective receptor port to the drug-dispensing nozzle.

8. The system of claim 1, wherein the drug delivery module comprises one or more nozzles, wherein each nozzle is configured to couple with a respective drug delivery port of the one or more drug delivery ports of the skin base, wherein each nozzle comprises a nozzle pin in fluid communication the piercing pin of a respective receptor port of the one or more receptor ports of the drug delivery module.

9. The system of claim 8, wherein the one or more receptor ports are arranged on a first side of the drug delivery module and the one or more nozzles are arranged on a second side of the drug delivery module, the second side arranged opposite to the first side.

10. The system of claim 9, wherein the second side of the drug delivery module is arranged facing the skin base.

11. The system of claim 10, wherein the second side of the drug delivery module is arranged facing a first side of the skin base, the skin base further comprising a second side opposite said first side of the skin base, wherein the second side of the skin base is configured to face a subject's skin.

12. The system of claim 11, wherein the second side of the skin base is configured to adhere to the subject's skin.

13. The system of claim 1, wherein the drug-dispensing nozzle comprises a needle.

14. The system of claim 1, wherein the drug delivery module comprises one or more retainer straps, wherein each retainer strap is attachable to the drug delivery module in a securing position in which said each retainer strap secures said respective container to the drug delivery module while the respective container is pierced by the piercing pin of a receptor port of the one or more rector ports.

15. The system of claim 14, wherein said one or more retainer straps are configured to further adopt a storage position in which the one or more retainer straps are detachably attached to an area of the drug delivery module separate from said one or more receptor ports.

16. The system of claim 14, wherein at least one retainer strap of said one or more retainer straps is stretchable, and further wherein said at least one retainer strap in the securing position is stretched to compress the respective container while the respective container is pierced by the piercing pin of a receptor port of the one or more receptor ports.

17. The system of claim 1, further comprising a body-securing strap configured to attach to a subject's body, wherein the skin base is carried by the body-securing strap.

18. A wearable drug delivery system for delivering one or more drugs to a subject's body, comprising:
    a skin base configured to attach to a subject's body, the skin base comprising a drug-dispensing nozzle and one or more drug delivery ports, wherein each drug delivery port is in fluid communication with the drug-dispensing nozzle via one or more channels formed in the skin base;

a drug delivery module disconnectably mountable to the skin base and comprising one or more receptor ports for the connection thereto of a respective container containing a drug, each receptor port comprising a piercing pin configured to pierce said respective container; wherein the drug delivery module and skin base are flexible and configured to conform to the subject's body; and an electronic control system comprising a control module and one or more electronically controlled valves operatively connected to the control module, wherein each electronically controlled valve is configured to regulate fluid communication from the piercing pin of a respective receptor port of the one or more receptor ports to the drug-dispensing nozzle responsively to a signal from the control module.

19. A wearable drug delivery system for delivering one or more drugs to a subject's body, comprising:

a skin base formed as a flexible panel configured to attach to a subject's body, the skin base comprising a drug-dispensing nozzle and one or more drug delivery ports, wherein each drug delivery port is in fluid communication with the drug-dispensing nozzle via one or more channels formed in the skin base;

a drug delivery module formed as flexible panel, the drug delivery module disconnectably mountable to the skin base and comprising one or more receptor ports for the connection thereto of a respective container containing a drug, each receptor port comprising a piercing pin configured to pierce said respective container; wherein the drug delivery module and skin base are flexible and configured to conform to the subject's body; and an electronic control system comprising a control module and one or more electronically controlled valves operatively connected to the control module, wherein each electronically controlled valve is configured to regulate fluid communication from the piercing pin of a respective receptor port of the one or more receptor ports to the drug-dispensing nozzle responsively to a signal from the control module.

\* \* \* \* \*